US00PP14108P39

(12) United States Plant Patent
Zipperer, III

(10) Patent No.: US PP14,108 P3
(45) Date of Patent: Aug. 26, 2003

(54) GLADIOLUS PLANT NAMED 'EURO BLANCA'

(76) Inventor: John O. Zipperer, III, 13590 Brynwood La., Ft. Myers, FL (US) 33912

( * ) Notice: Subject to any disclaimer, the term of this patent is extended or adjusted under 35 U.S.C. 154(b) by 0 days.

(21) Appl. No.: 09/918,663

(22) Filed: Jul. 31, 2001

(65) Prior Publication Data

US 2003/0028944 P1 Feb. 6, 2003

(51) Int. Cl.[7] ..... A01H 5/00

(52) U.S. Cl. ..... Plt./301
(58) Field of Search ..... Plt./301

*Primary Examiner*—Bruce R. Campell
*Assistant Examiner*—Anne Marie Grúnberg
(74) *Attorney, Agent, or Firm*—Hahn Loeser & Parks LLP; Laura G. Barrow

(57) ABSTRACT

A new and distinct gladiolus variety, designated 'Euro Blanca', is shown and described. The variety is characterized as having a long flower head, high number of florets and a heavy stem. The color of the bloom tight is Green White Group 157A, of the bloom open perfect condition is Greyed White Group 156D, and open going down is Greyed White Group 156C.

2 Drawing Sheets

The present invention comprises a new and distinct variety of a *Gladiolus l.* referred to by the variety name 'Euro Blanca.'

BRIEF DESCRIPTION OF THE PHOTOGRAPHS

FIG. 1 is a photograph of a 'Euro Blanca' variety plant in bloom.

ASEXUAL REPRODUCTION

Figure 2:
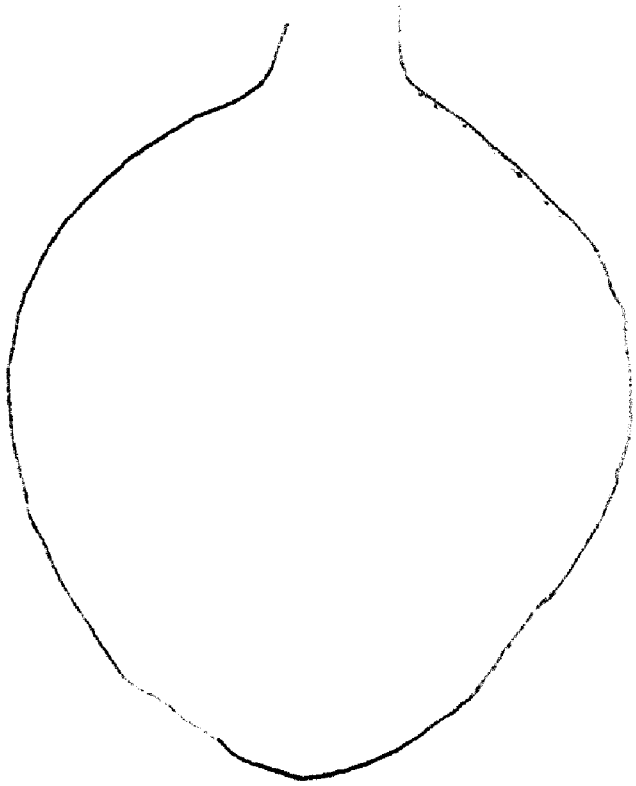
FIG. 2 is a drawing illustrating the shape and size of the large petals.

The new variety was originated by the Applicant in a controlled proprietary breeding program in Ft. Myers, Fla. wherein selected gladiolus varieties were crossed (the Applicant's selected provisional breeder's designation is 38-1). The female parent was a white gladiolus variety named 'T-200,' an unpatented, released variety by Turk characterized in part by having a harvesting time similar to the 'White Friendship' gladiolus variety, 16 to 18 florets, and lightweight stems. The male parent was a green gladiolus variety named 'T-815,' an unpatented released variety characterized in part by having a long head, small blooms, and with blooms that die soon after opening. The 'T-815' parent variety is the most similar to the 'Euro Blanca' variety described herein. The seeds were planted in Ft. Myers, Fla., and the selection of the 'Euro Blanca' variety was made in Spring 1988. Asexual reproduction of the 'Euro Blanca' variety was achieved by collecting cormels from the first corm and growing said cormels to maturity in Ft. Myers. All subsequent asexual reproductions of the 'Euro Blanca' variety remain true to the original variety type.

BOTANICAL DESCRIPTION

The accompanying color photograph (FIG. 1) shows the inflorescence and various stages of blooming of the 'Euro Blanca' variety plant.

The following botanical description, except for color, of the 'Euro Blanca' variety was observed when the plant was 83 days old grown under the following conditions in Ecuador:

1) Twelve-hour daylight days with high light intensity;
2) Temperatures: 58–60° F. (low's) and 69–75° F. (high's);
3) Humidity: 50–55%
4) Rainfall: 2–3 inches/month.

All color descriptions with respect to parts of the variety, where color is a distinguishing feature, are made to The Royal Horticultural Society Colour Chart (R.H.S.), except where terms of ordinary usage and dictionary meaning are used. Color observations with respect to The R.H.S. Colour Chart were made in the Netherlands under similar environmental conditions as described above, but at increased day lengths of 12 to 17 hours and 50% to 65% humidity.

The spike of the plant is about 147 cm and contains 18–19 florets when grown from #2 size corms (i.e. 1.25 to 1.50 inches) in Ecuador. The stem color is Yellow Green Group 144C with a stem diameter of 1.4 cm. The head length is about 50 cm, and the bloom diameter is 10 cm. It should be noted, however, that various factors will affect spike length, including temperature (larger spikes occur in cooler weather), irrigation, light intensity, fertilization, soil type (larger spikes occur in heavy soils versus sandy soil), and bulb size (larger bulbs result in larger spikes).

The leaf color of the 'Euro Blanca' variety is Green Group 138A. The leaf size is about 90 cm (length) by 5 cm (width).

The bud size of the 'Euro Blanca' variety is about 6.5 cm in length. The flowers of the variety each consist of a total of six petals, the most common petal arrangement consisting of three large petals, two medium petals, and one small petal. In this arrangement, observed in Florida, the large petals are located on the top half of the bloom, normally between 10:00 and 2:00 (referring to a clock face). The medium petals are found on the bottom half of the bloom, usually between 4:00 and 8:00, while the small petal is typically located between 5:00 and 7:00 near the bottom of the bloom. Another common petal arrangement (observed in Florida) also consists of three large petals located on the top half of the bloom between 10:00 and 3:00, but with one medium petal located on the lower half of the bloom (between 4:00 and 8:00) and two small petals on the lower half of the bloom (between 7:00 and 8:00). A third petal arrangement of the variety (observed in The Netherlands) consists of five large petals and one small petal located on the lower half of the flower (i.e. at about 6:00). The color of the bloom tight is Green White Group 157A. The color of the bloom open perfect condition is Greyed White Group 156D, and the color open going down is Greyed White Group 156C.

The variety has three stamens and one pistil. The color of the pistil (head and stem) is White Group N155A. The stamen stem color is also White Group N155A; however, the stamen head has a Red Group36B color on the pollen-producing side.

If a tight cut stem, with one floret showing color, is placed in water, the first bloom will be fully open in three days. The bloom will last for 2.5 days, and the stem will finish blooming eleven days after being placed in water.

The corms of the 'Euro Blanca' variety are typical for the gladiolus, and have a Yellow Orange Group 14B color under the husk on the top of the bulb one day after harvest.

GENERAL OBSERVATIONS

The 'Euro Blanca' variety takes about 83 days to harvest in Ecuador, which is about seven days longer than the 'T-200' gladiolus variety. Unlike the 'T-200' variety, the 'Euro Blanco' variety provides excellent growth in mid-winter days of 10.5 hours. Tests conducted by the inventor have shown that the 'Euro Blanca' variety, like the 'T-200' variety, has good tolerance to high temperatures.

The 'Euro Blanca' variety has normal resistance to Curvalaria and Botrytis foliar diseases, but is susceptible to attack by Fusarium species.

The variety does not emit a fragrance.

The variety usually produces one to two stems per #2 size corm. The variety can hold open 5–6 blooms after shipping one week in a box. Compared to the parent 'T-200' variety, the 'Euro Blanco' variety is 15–20 cm taller, has one to two more florets per flower head, and has a larger stem diameter (i.e. 0.4 cm larger). The bloom diameter of 10 cm is similar to that of the 'T-200' variety.

When compared to the parent 'T-815' variety, the 'Euro Blanca' variety is similar in many respects. For example, both varieties have long flower heads with a high number of florets and a heavy stem. The bloom size of the 'Euro Blanca' variety is only slightly larger. Time to harvest both varieties are nearly identical. 'Euro Blanca', however, produces very long stems that are 10–15 cm longer than the stems of the 'T-815' variety. 'T-850' has poor quality blooms in that the plant cannot hold open more than three blooms at the same time, unlike 'Euro Blanca', which can hold open five to six blooms. The foliage of the 'T-815' variety has a darker green color compared to the claimed variety. Finally, the bloom of the 'T-815' is a light green color compared to 'Euro Blanca', which has a greyed white color, as described above.

I claim:

1. A new and distinct gladiolus variety of plant, 'Euro Blanca', as shown and described herein.

* * * * *